(12) United States Patent
Tepic et al.

(10) Patent No.: US 10,159,576 B2
(45) Date of Patent: Dec. 25, 2018

(54) TROCHLEAR GROOVE PROSTHESIS

(75) Inventors: Slobodan Tepic, Zurich (CH); Jacek DeHaan, Winter Park, FL (US)

(73) Assignee: Kyon AG, Zurich (CH)

( * ) Notice: Subject to any disclaimer, the term of this patent is extended or adjusted under 35 U.S.C. 154(b) by 159 days.

(21) Appl. No.: 13/265,092

(22) PCT Filed: Apr. 19, 2010

(86) PCT No.: PCT/US2010/031657
§ 371 (c)(1),
(2), (4) Date: May 1, 2012

(87) PCT Pub. No.: WO2010/123836
PCT Pub. Date: Oct. 28, 2010

(65) Prior Publication Data
US 2012/0209395 A1   Aug. 16, 2012

Related U.S. Application Data

(63) Continuation of application No. 12/426,249, filed on Apr. 19, 2009, now abandoned.

(51) Int. Cl.
*A61F 2/38* (2006.01)
*A61F 2/30* (2006.01)

(52) U.S. Cl.
CPC ........ *A61F 2/3877* (2013.01); *A61F 2/30767* (2013.01); *A61F 2002/30892* (2013.01); *A61F 2002/30934* (2013.01)

(58) Field of Classification Search
USPC ............ 623/20.14, 20.18, 20.19, 20.2, 20.35
See application file for complete search history.

(56) References Cited

U.S. PATENT DOCUMENTS

| | | | |
|---|---|---|---|
| 4,479,271 A | 10/1984 | Bolesky et al. | |
| 5,702,459 A | 12/1997 | Hummer et al. | |
| 6,616,696 B1* | 9/2003 | Merchant | 623/20.18 |
| 7,582,118 B2* | 9/2009 | Brown | A61F 2/3877 623/20.17 |
| 2004/0236428 A1* | 11/2004 | Burkinshaw | A61F 2/3877 623/20.15 |
| 2005/0102032 A1* | 5/2005 | Beynnon | A61F 2/38 623/20.35 |
| 2006/0178748 A1* | 8/2006 | Dinger et al. | 623/18.11 |
| 2007/0173946 A1 | 7/2007 | Bonutti | |
| 2007/0288021 A1* | 12/2007 | Rickels | A61B 17/1764 606/916 |
| 2008/0188942 A1* | 8/2008 | Brown | A61F 2/3877 623/20.15 |

* cited by examiner

*Primary Examiner* — David Isabella
*Assistant Examiner* — Christine Nelson
(74) *Attorney, Agent, or Firm* — Occhiuti & Rohlicek LLP

(57) ABSTRACT

A trochlear groove prosthesis includes a base plate and cap. The base plate and cap are shaped to correspond to the shape of the trochlear groove. A cut is made in the femur to remove the worn or damaged trochlear groove. The base plate is attached to the cut portion of the femur. The cap is mated with the base plate. The prosthesis and procedure provide a properly shaped prosthesis with a single planar cut of the femur.

21 Claims, 6 Drawing Sheets

TROCHLEAR GROOVE PROSTHESIS

CROSS-REFERENCE TO RELATED APPLICATIONS

The present application is a U.S. national phase application, filed in accordance with 35 U.S.C. § 371, of International Application No. PCT/US2010/031657, which was filed Apr. 19, 2010, and which claims the benefit of the filing date of U.S. patent application Ser. No. 12/426,249, which was filed Apr. 19, 2009 (now abandoned).The content of these priority applications is hereby incorporated by reference herein its entirety.

TECHNICAL FIELD (Field of the Invention)

The present invention relates to prostheses for joints. More particularly, it relates to a prosthesis for a portion of the femur to correct wear of the throchlear groove.

BACKGROUND OF THE INVENTION

Joints of animal and human bodies are miraculous mechanical devices. They often last a lifetime with no added lubrication or service. However, the joints, like any mechanical or biological structure, are subject to certain failures. The joints are naturally lubricated and cushioned by synovial membranes and cartilages so that they normally appear subject to little wear. Part of this apparent lack of wear is doubtless due to living tissue's ability of regeneration and self-repair. However, joints are not invincible. Sometimes the body's immune system goes awry and attacks a joint, thereby damaging it irreversibly (rheumatoid arthritis). Sometimes old age and general wear and tear catches up with the joint's biological repair system (osteoarthritis). Sometimes a sharp blow or overextension of the joint results in mechanical damage that cannot be repaired by the normal healing process.

The knee joint in animals and humans is a frequent place for joint damage. The knee is a common source of problems because the joint has an unusually large range of motion and bears the weight of the entire body.

This wide range of motion requires extensive contact surface between the femur and the tibia. The joint is rather loosely held together by tendons and ligaments to permit such a wide range of motion. A front-facing side of the knee joint is protected by a separate knee cap (patella) which is held in place by ligaments and slides on a femoral joint surface (trochlear groove) as the knee bends. The patella and its ligaments are mechanically involved in joint extension. If any of the joint surfaces (femoral surface, patellar surface, or tibial surface) becomes damaged or roughened, the knee joint will not operate properly. Damage to the knee can cause pain and/or affect the ability to walk. Changes in operation of the knee from damage can cause further deterioration of the joint. Furthermore, changes in gait caused by adjustments to the damaged knee can result in additional stresses on and damage to other joints.

A common problem is damage to the patello-femoral joint so that free motion of the patella is inhibited and painful. This joint is particularly susceptible to repetitive damage. Dislocation of the knee cap can cause damage or unexpected wear to the edges of the trochlear groove. This makes the subsequent dislocations more probable. Additionally, in some people and animals, their gait may cause uneven wear on the edges of the trochlear groove so that one side becomes more worn. Thus, the knee cap fails to remain in position.

Such damage is illustrated in FIGS. 1 and 2a-2c. For purposes of illustration, the failure of the trochlear groove is illustrated in connection with the knee of a dog. Although the specific geometry of the knee joints in humans and other animals varies, the main components and relationships are the same across all knee joints. Therefore, the problems, and the solutions provided in the present invention, are equally applicable to prosthesis of humans and different animals. FIG. 1 illustrates a typical knee joint 1. Only the elements of the joint relevant to its operation in connection with the present invention are shown. The knee joint 1 includes the femur 2, tibia 3 and patella 4. The patella 4 is positioned in front of the condyles of the femur 2 and glides within the trochlear groove 6. Patellar ligament 5 is connected from the tibia 3 to the quadriceps tendon 7 across the patella 4 to keep the patella 4 in place.

FIGS. 2a-2c illustrate a cross section of the knee joint along the A-A plane in FIG. 1. FIG. 2a illustrates a normal femur 2 having a pronounced trochlear groove 6. The medial side 21 of the femur has an extension 23 on the medial side of the trochlear groove 6. Similarly, an extension 24 of the lateral side 22 of the femur is positioned on the lateral side of the trochlear groove 6. The trochlear groove 6 itself has a unique shape to retain the patella 4 in position and to allow for proper movement of the patella 4 on the femur 2. Damage may occur to the extensions 23, 24 of the medial 21 and lateral 22 sides of the femur, as illustrated in FIGS. 2b and 2c respectively. If medial side extension 23' is damaged or excessively worn (FIG. 2b), the patella 4 can slide 4' off the medial side 21 of the femur. In fact, operation of forces on the knee will likely cause such motion and may cause further damage to the medial side extension 23'. Similarly, excessive wear or damage to the lateral side extension 24' (FIG. 2c) will cause the patella 4 to slide 4" off the lateral side 22 of the femur.

Such damage can make normal joint movement almost impossible. At one time, before the mechanical and protective functions of the patella were understood, the patella was simply removed in an attempt to cure patello-femoral problems. Today, a variety of prosthetic replacements have been developed for different joint surfaces of the knee joint. In extreme cases the entire joint can be replaced with a prosthetic device. However, such surgery naturally requires a considerable time for recovery. In less extreme cases it may be advantageous to replace only the damaged part of the joint. Generally, correction of the patello-femoral joint requires extensive replacement of portions of the femur, including the portions contacting the tibia. Furthermore, such prosthesis merely provide a through to limit lateral movement of the patella. They fail to replicate the unique shapes of the trochlear groove so that correct operation of the joint is achieved.

U.S. Pat. No. 3,806,961 to Miller shows a prosthesis having mating femur and patella parts. An annular sector having a guide groove is implanted into the end of the femur. A raised arcuate runner member is implanted into the patella so that the patella can slidably move in the guide groove with the runner member acting as a bearing surface. The prostheses are attached to the bone surfaces by bone cement.

U.S. Pat. No. 3,878,566 to Bechtol discloses another patellar prosthesis. Here a femoral implant bears a more or less acute groove, and the patellar component bears a somewhat crest-like ridge projection that rides in the groove. U.S. Pat. No. 4,007,495 to Frazier uses a slightly different approach. The patellar component rides in a femoral groove, but the system is also equipped with a femoral projection that engages a slot in the patellar implant. While this structure prevents separation of the patella from the femur, it also greatly restricts movement of the patella and may result in unnatural joint action.

U.S. Pat. No. 4,151,615 to Hall provides a femoral component and a patellar component that more closely approximate natural patello-femoral joint motion.

U.S. Pat. No. 4,838,891 to Branemark et al. addresses the adhesion problems of prior prostheses by providing a two-part system where an anchoring device is inserted during a first operation. After the healing process fixes the anchoring device firmly in place, a second operation inserts the weight-bearing part of the prosthesis which engages the anchoring device. However, this system requires multiple operations even to insert a simple patello-femoral prosthesis.

U.S. Pat. No. 5,824,098 to Stein replaces the femoral surface of the patella with a convex prosthesis of a low friction material. The trochlear groove is replaced with an elongated femoral prosthesis having an arcuate indentation on its upper surface to receive the patella prosthesis.

All of these prior art prostheses require extensive surgery to access all parts of the patella and femur. They require extensive removal of portions of the femur, which may include sound material. They cause alteration of the operation of the patello-femoral joint. Therefore, a need exists for a simple prosthesis for replacing only the trochlear groove with minimally invasive surgery.

DISCLOSURE OF INVENTION

The present invention provides a prosthesis and method for installation which simplifies replacement of the trochlear groove when other portions of the knee joint remain sound. According to one aspect of the invention, a trochlear joint prosthesis includes a base plate and a cap. The base plate and cap are shaped similar to the shape of the trochlear groove. The base plate is planar and is configured to be attached to a flat face of the femur. The cap and base plate are configured to mate so that the cap is retained in position with respect to the base plate. According to one aspect of the invention, the cap includes a plurality of pegs extending from the bottom thereof. The base plate includes a plurality of holes which mate with the pegs on the cap.

According to another aspect of the invention, the base plate includes a plurality of holes to promote bone ingrowth. According to another aspect of the invention, the base plate is formed of a material for promoting bone growth. According to another aspect of the invention, the base plate is coated to promote bone growth.

According to another aspect of the invention, the cap is formed of a low friction material. According to another aspect of the invention, the cap is coated with a low friction material. According to another aspect of the invention, a low friction surface is formed on the cap.

According to another aspect of the invention, a minimally invasive procedure is used to install a trochlear groove prosthesis. The method of the present invention may be used with the prosthesis hereof. However, the method may be used with other types of prostheses which can be utilized with this method. According to one aspect of the procedure, the ligaments and muscles on one side of the knee are moved to expose the trochlear aspect of the femur. A transverse cut is made in the femur to remove the trochlear groove. The cut bone is removed without disturbing the patella. The prosthesis is installed on the cut portion of the femur. According to another aspect of the invention, the prosthesis is installed by attaching a base plate to the cut portion of the femur and a cap is mated with the base plate. According to another aspect of the invention, the base plate is attached to the femur with screws.

BEST MODE FOR CARRYING OUT THE INVENTION

Figure 5:
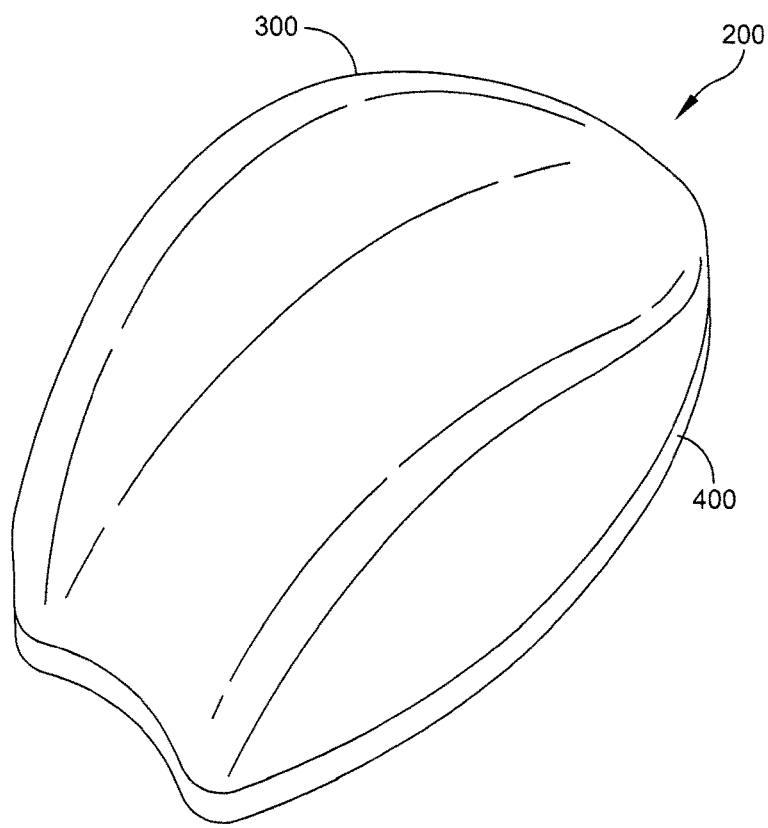
FIG. 5 is a perspective view of a trochlear groove prosthesis according to an embodiment of the present invention.

The present invention provides a prosthesis for a worn or damaged trochlear groove when other portions of the femur and patella remain sound. The prosthesis of the present invention can be installed without separating the entire knee joint. As illustrated in FIG. 5, a prosthesis 200 according to an embodiment of the invention includes two parts, a base plate 400 and a cap 300. The base plate 400 is attached to a prepared portion of the femur 2 below the patella 4. The cap 300 mates with the base plate so as to be retained in position. The cap 300 has an upper arcuate surface formed to correspond to the shape of the trochlear groove.

Figure 1:
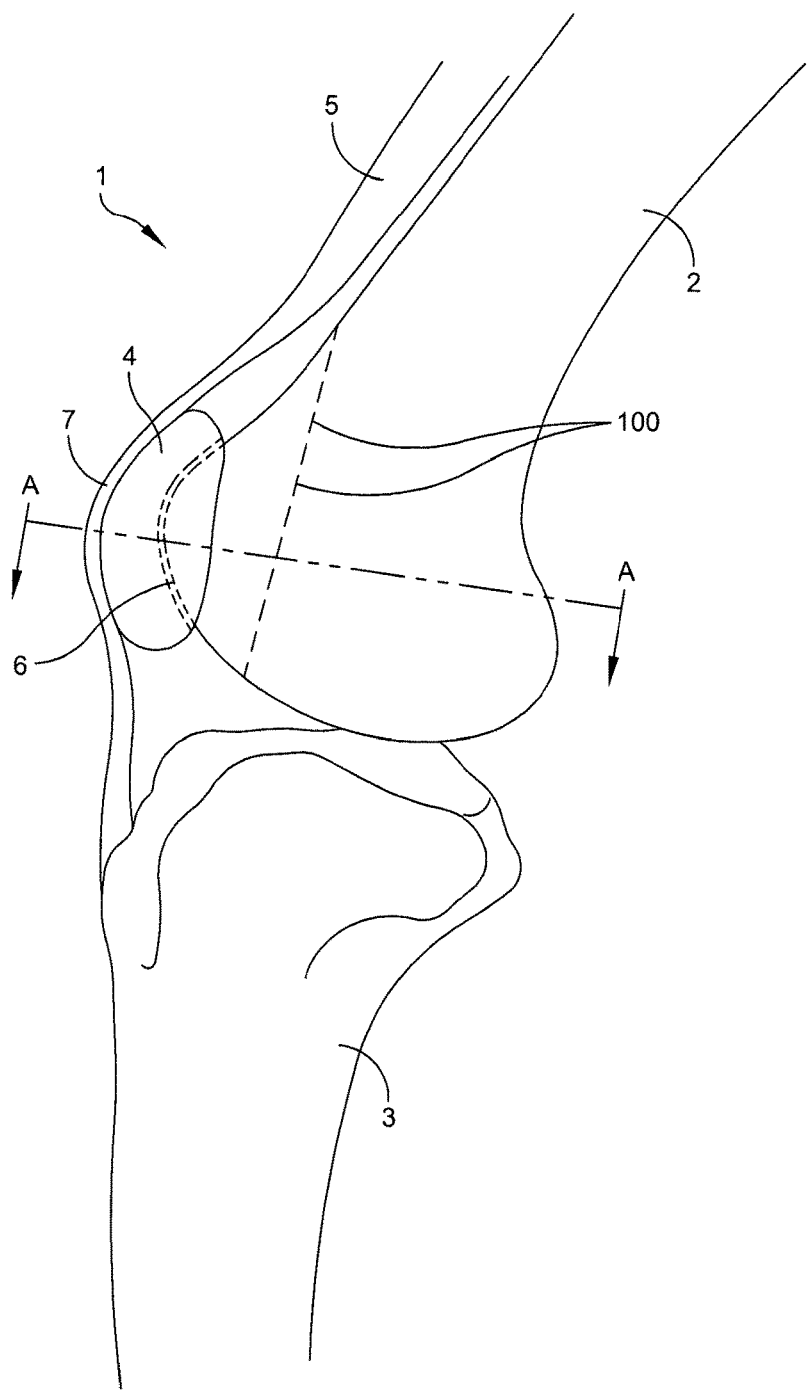
FIG. 1 is a side view of a typical canine knee joint.
Figure 2A:
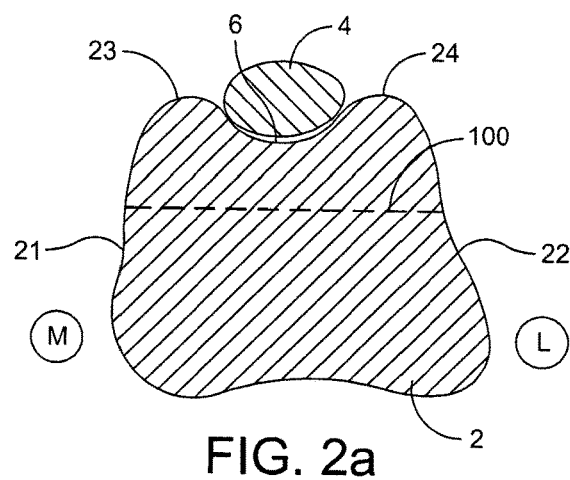
FIGS. 2a-2c are cross sectional views of the patello-femoral joint showing different types of wear or damage.
Figure 2B:
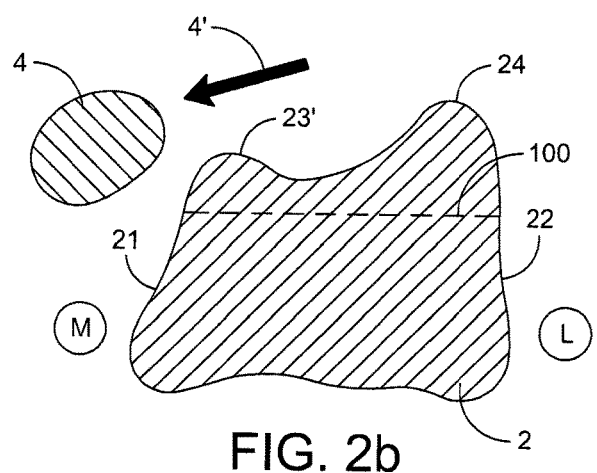
Figure 2C:
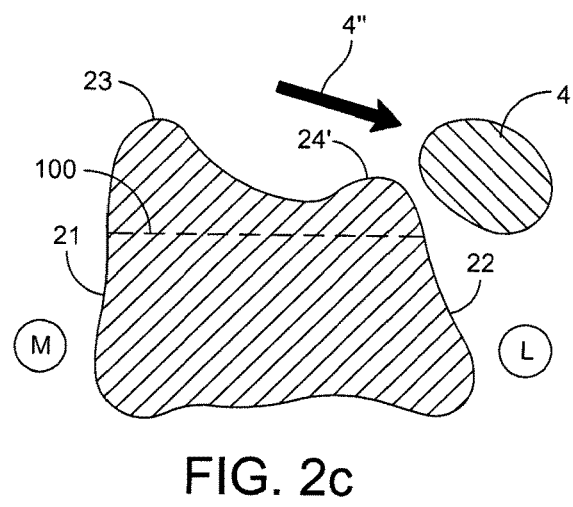
Figure 3:
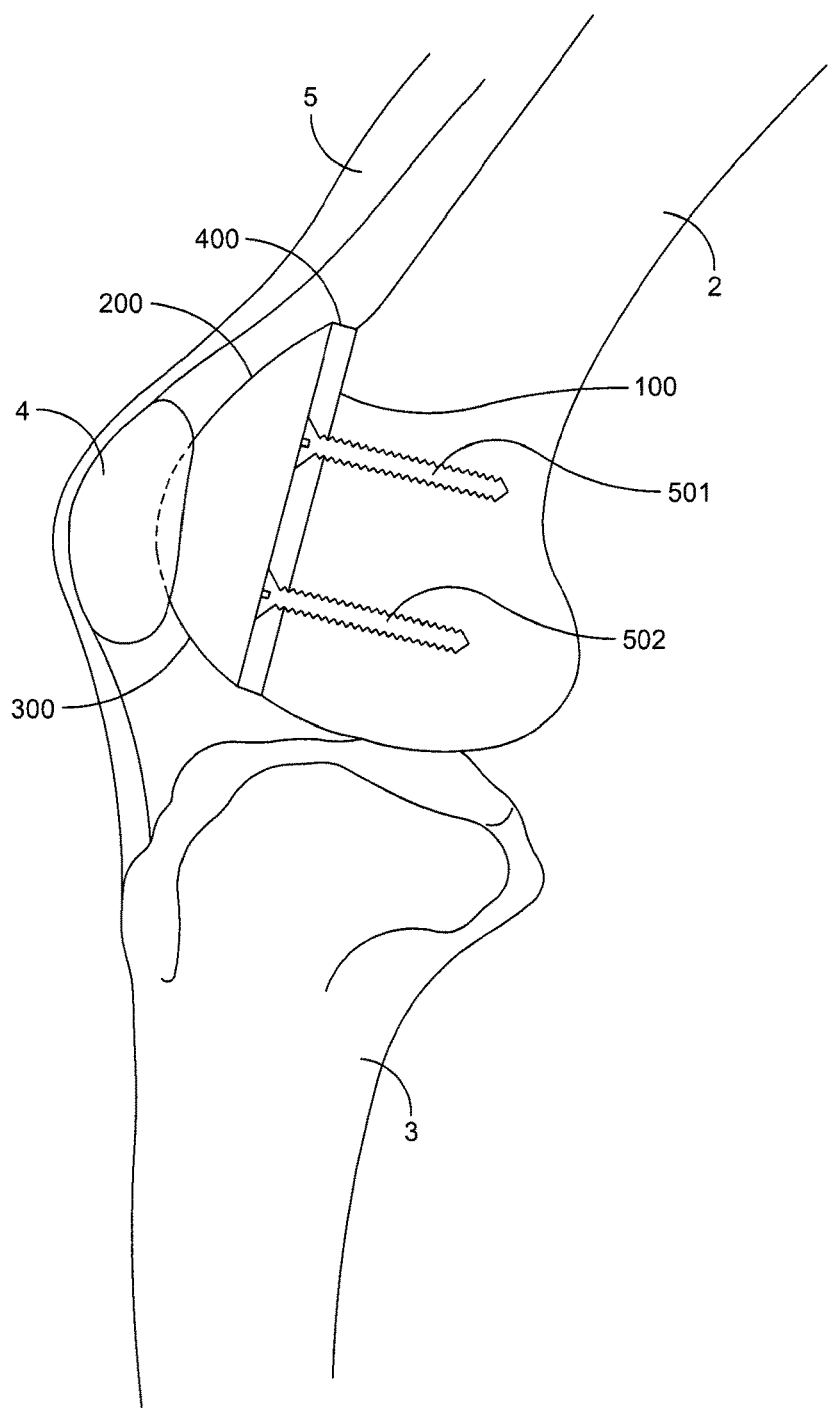
FIG. 3 is a side view of a canine knee joint including a trochlear groove prosthesis according to an embodiment of the present invention.

In order to install the trochlear groove prosthesis of the present invention, a straight cut 100 is made along the head of the femur, as shown in FIG. 1. The cut 100 removes the damaged portion of the trochlear groove. As illustrated in FIGS. 2a-2c, the cut 100 is positioned below the worn portion of the medial or lateral extension 23', 24'. The cut 100 provides a flat surface on the face of the femur 2 for attachment of the prosthesis. In order to make the cut 100, the muscles and ligaments on only one side of the knee must be moved out of the way or removed, so that the bone can be accessed. Disassembly of the knee joint and detachment of the patella ligament 5 is not necessary in order to make the cut or to install the prosthesis.

Figure 4:
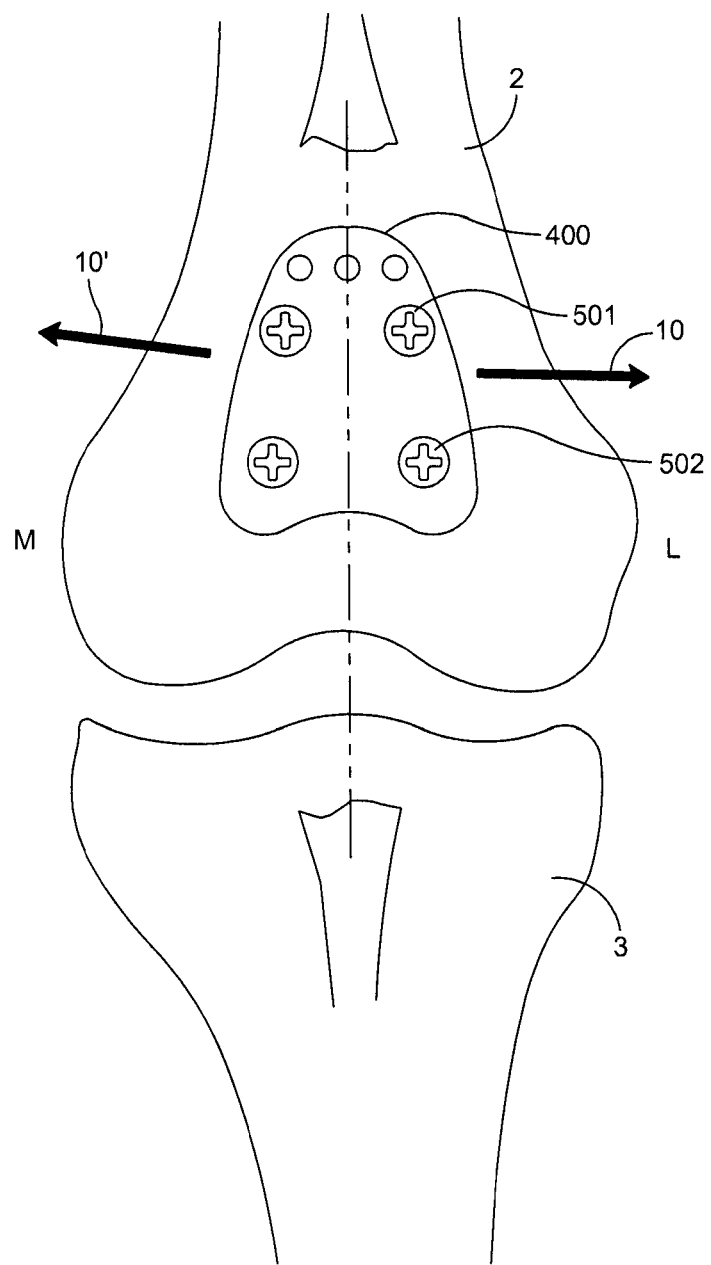
FIG. 4 is a front view of a portion of a canine knee joint including a base plate for a trochlear groove prosthesis according to an embodiment of the present invention.

After the femur has been cut, the base plate 400 is positioned on the flat space created by the cut 100. As illustrated in FIG. 4, the position of the base plate 400 can be adjusted laterally 10 or medially 10' so that the trochlear groove of the prosthesis is properly aligned with the patella ligament. The base plate 400 is attached to the femur 2 with screws 501, 502. Since the cut 100 only removes the surface of the femur, substantial bone remains for firmly attaching the base plate 400 with the screws 501, 502. After the base plate 400 is attached, the cap 300 is placed on the base plate. The cap 300 and base plate 400 mate so that the cap 300 is held in position. The patella 4 is then positioned within the groove on the cap 300 and any ligaments and muscles are reattached and/or returned to their proper positions.

Figure 6:
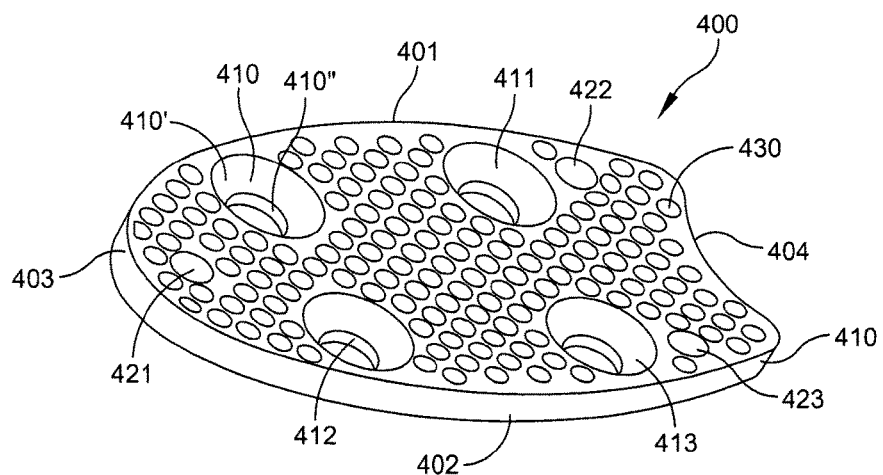
FIG. 6 is a prospective view of a base plate of a trochlear groove prosthesis according to an embodiment of the present invention.

FIG. 6 illustrates an embodiment of a base plate 400 for the trochlear groove prosthesis of the present invention. The base plate 400 is a planar piece of material. The base plate 400 may be formed of any material for implantation in a human or animal body. Preferably, it is of a material which provides good adhesion with the bone. According to an embodiment, the base plate 400 is of a metal. It may be shaped or coated for bone ingrowth or ongrowth. According to an embodiment of the invention, a plurality of small through holes 430 are positioned over the surface of the base plate 400 to allow for bone ingrowth or ongrowth. Four screw holes 410, 411, 412, 413 are symmetrically positioned for attaching the base plate 400 to the bone of the femur 2. Of course, any number of and positions for the screw holes may be used. In the embodiment of FIG. 6, each of the screw holes 410 includes a countersink portion 410' and straight portion 410". As is known with prostheses, this allows the screws to be recessed to the level of the upper surface of the base plate 400.

The base plate 400 has a shape which is representative of the shape of the femur 2 which results from the cut 100. It includes two arcuate sides 401, 402, a narrow, rounded top end 403 and a concave base 404. Three holes 421, 422, 423 are used for positioning the cap 300 on the base plate 400. These holes 421, 422, 423 may be conic in shape. Of course, any number of holes could be used.

Figure 7A:
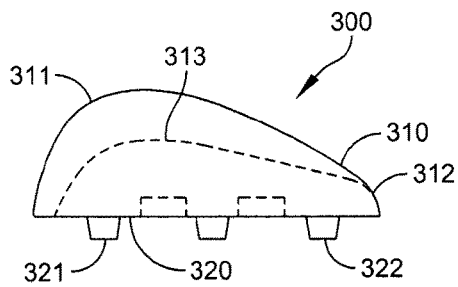
FIGS. 7a-7c are side, end, and bottom views respectively of a cap of a trochlear groove prosthesis according to an embodiment of the present invention.
Figure 7B:
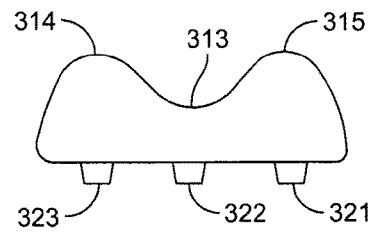
Figure 7C:
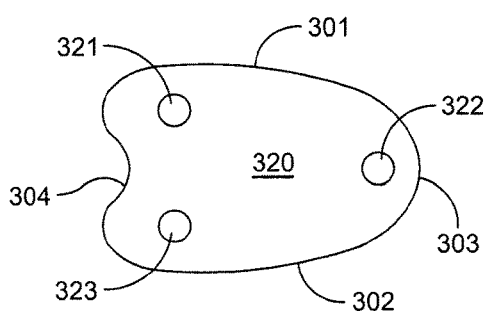

A cap 300 according to an embodiment of the invention is illustrated in different views in FIGS. 7a-7c. The cap 300 includes a planar bottom 320 and a arcuate top 310. A plurality of pegs 321, 322, 323 extend from the planar bottom 320. The pegs 321, 322, 323 may be formed with the cap 300 or may be attached to the cap 300. The pegs 321, 322, 323 are shaped to mate with the holes 421, 422, 423 in the base plate 400 for positioning the cap 300 on the base plate 400. The shape of planar bottom 320 of the cap 300 is similar to that of the base plate 400. It includes two arcuate sides 301, 302, a narrow, rounded top end 303 and a concave base end 304. The top 310 of the cap 300 has a shape similar to that of the trochlear groove. It includes shorter portion 312 at the rounded top end 303 and a taller portion 311 towards the base end 304. A center groove 313 is formed between extensions 314, 315 on the sides of the cap 300. As with the base plate, the cap may be formed of any material for implantation. Preferably, it is of a polished metal. It may include a coating to provide a low friction surface on which the patella can slide.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

What is claimed is:

1. A trochlear groove prosthesis comprising:
   a planar base plate configured to be attached to a flat face of a femur that was generated by surgically removing a damaged portion of the trochlear groove, wherein the planar base plate includes a planar bottom surface, defining a single plane, configured to be placed on the flat face of the femur; and
   a cap that has a flat lower surface that mates with the base plate and an upper surface comprising side extensions forming a central groove, the upper surface defining a shape similar to a non-damaged shape of a non-damaged trochlear groove of the femur such that the upper surface is configured to receive a patella for movement along the central groove defined by the side extensions of the upper surface of the cap without the patella sliding outside the side extensions.

2. The prosthesis of claim 1, wherein the base plate has a shape, when viewed from the bottom, corresponding to a shape of a femur from which a trochlear groove has been removed.

3. The prosthesis of claim 1, wherein the base plate is configured to mate with and retain the cap by containing a plurality of holes therein; and wherein the cap includes a plurality of pegs extending from the flat lower surface thereof that fit within the plurality of holes in the base plate.

4. The prosthesis of claim 1, wherein the base plate is shaped or coated to promote bone ingrowth or ongrowth.

5. The prosthesis of claim 1, wherein the cap is formed of a low friction material.

6. The prosthesis of claim 1, wherein at least a portion of the upper surface of the cap is coated with a low friction material.

7. The prosthesis of claim 1, wherein a low friction surface is formed on the upper surface of the cap.

8. A method for implanting the prosthesis of claim 1 in the knee, the method comprising the steps of:
   making a planar cut in a femur below a patella to remove the trochlear groove;
   installing the prosthesis onto the planar cut; and
   positioning the patella on the upper surface of the prosthesis.

9. The method of claim 8, wherein the installing step includes the steps of:
   installing the base plate onto the planar cut; and
   mating the cap to the base plate.

10. The method of claim 9, wherein the step of installing the base plate includes the step of inserting at least one screw through the base plate into the femur.

11. The method of claim 8 further comprising, before the step of making the planar cut, the step of moving ligaments and muscles on one side of a knee to expose a trochlear aspect of the femur.

12. The prosthesis of claim 1, wherein the base plate has a perimeter shape representative of the shape of the femur following surgical removal of the damaged portion of the trochlear groove, the shape comprising two arcuate sides, a narrowed, rounded top end, and a concave base end.

13. The prosthesis of claim 1, wherein the base plate comprises screw holes.

14. The prosthesis of claim 13, wherein the screw holes comprise a countersink portion and a straight portion.

15. The prosthesis of claim 1, wherein the base plate is metal.

16. The prosthesis of claim 4, wherein a plurality of small through holes are positioned over the surface of the base plate to allow for bone ingrowth or ongrowth.

17. The prosthesis of claim 1, wherein the cap comprises a polished metal.

18. The prosthesis of claim 1, wherein the cap comprises two arcuate sides, a narrowed, rounded top end, and a concave base end.

19. The prosthesis of claim 1, wherein the planar base plate includes a plurality of screw holes extending from the upper surface of base plate to the planar bottom surface of the base plate, the plurality of screw holes configured to receive screws for attaching the base plate to the flat surface of femur.

20. The prosthesis of claim 19, wherein each of the plurality of screw holes is structured to include a countersink portion and a straight portion to receive screws recessed to the upper surface of the base plate.

21. The prosthesis of claim 1, wherein the planar base plate comprises a plurality of holes extending from the upper surface of the base plate to the bottom surface of the base plate to promote bone ingrowth or ongrowth, wherein the plurality of holes are covered by the flat lower surface of the cap when the cap is mated with the base plate.

* * * * *